United States Patent
Oshimura

(10) Patent No.: US 6,656,892 B2
(45) Date of Patent: Dec. 2, 2003

(54) DETERGENT COMPOSITION

(75) Inventor: Eiko Oshimura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/121,840

(22) Filed: Apr. 15, 2002

(65) Prior Publication Data

US 2003/0069163 A1 Apr. 10, 2003

(30) Foreign Application Priority Data

Apr. 24, 2001 (JP) .................................. 2001-125816

(51) Int. Cl.$^7$ .............................. C11D 1/10; C11D 1/94; C11D 1/90; C11D 3/37
(52) U.S. Cl. ................. 510/124; 510/123; 510/125; 510/127; 510/130; 510/137; 510/138; 510/155; 510/158; 510/159; 510/490; 510/499; 424/70.11; 424/70.24; 424/70.27
(58) Field of Search ................. 510/123, 125, 510/127, 130, 137, 138, 155, 158, 159, 490, 499, 124; 424/70.11, 70.24, 70.27

(56) References Cited

U.S. PATENT DOCUMENTS

| | | | |
|---|---|---|---|
| 3,962,418 A | | 6/1976 | Birkofer ........................ 424/70 |
| 4,578,216 A | | 3/1986 | Fujii et al. |
| 4,915,863 A | * | 4/1990 | Aoyagi et al. ............... 252/102 |
| 5,607,678 A | | 3/1997 | Moore et al. |
| 5,648,323 A | | 7/1997 | Coffindaffer et al. |
| 5,712,232 A | * | 1/1998 | Moriyama et al. ........... 510/120 |
| 5,770,556 A | | 6/1998 | Farrell et al. ................ 510/447 |
| 6,284,230 B1 | * | 9/2001 | Sako et al. ............... 424/70.11 |
| 6,323,166 B1 | * | 11/2001 | Kamiya ........................ 510/119 |
| 6,333,301 B1 | * | 12/2001 | Kamiya ........................ 510/438 |
| 6,468,514 B2 | * | 10/2002 | Schmucker et al. ...... 424/70.19 |

FOREIGN PATENT DOCUMENTS

| | | |
|---|---|---|
| GB | 2 245 585 | 1/1992 |
| JP | 60-20363 | 5/1985 |
| JP | 1-178597 | 7/1989 |
| JP | 1-294799 | 11/1989 |
| JP | 6-264090 | 9/1994 |
| JP | 9-506351 | 6/1997 |
| WO | WO 91/14759 | 10/1991 |
| WO | WO 95/02388 | 1/1995 |
| WO | WO 95/15150 | 6/1995 |
| WO | WO 96/05798 | 2/1996 |
| WO | WO 96/37588 | 11/1996 |
| WO | WO98/29094 * | 7/1998 |
| WO | WO 98/55092 | 12/1998 |
| WO | WO 00/11124 | 3/2000 |
| WO | WO 00/71241 | 11/2000 |
| WO | WO 01/19946 | 3/2001 |

OTHER PUBLICATIONS

SOFW Journal, vol. 120, p. 854, "HAARKOSMETIK", 1994.

* cited by examiner

Primary Examiner—Gregory Delcotto
(74) Attorney, Agent, or Firm—Oblon, Spivak, McClelland, Maier & Neustadt, P.C.

(57) ABSTRACT

A detergent composition comprising (A) 5 to 30% by weight of at least one kind of surfactant selected from the group consisting of an anionic surfactant, an amphoteric surfactant, and a nonionic surfactant based on the total weight of the composition; (B) 0.1 to 5% by weight of a substance selected from the group consisting of an N-long-chain acyl acidic amino acid and a salt thereof based on the total weight of the composition; and (C) less than 0.2% by weight of a cationic polymer compound based on the total weight of the composition. The detergent composition provided has good foaming property and causes no friction during rinsing, as well as has excellent feeling of use by imparting moistness without tackiness to skin and providing good hair control without stiffness.

21 Claims, No Drawings

DETERGENT COMPOSITION

FIELD OF INVENTION

The present invention relates to a detergent composition. More specifically, the present invention relates to a detergent composition having excellent foaming property and is free from squeak during rinsing. More specifically, the present invention relates to a detergent composition with excellent feeling of use, for example, by imparting moistness without tackiness to skin and providing good hair control while suppressing stiffness.

RELATED ART

Good foaming property and high cleansing effect have conventionally been focused as performances of a main active agent contained in a detergent for application to a body or hair. In order to meet these requirements, sulfate ester type surfactants such as alkylsulfates and polyoxyethylene alkyl ether sulfates, higher fatty acid salts and polyoxyethylene alkyl ether acetates have been widely used.

In order to suppress rough skin feel during rinsing and imparting moist and soft finish to skin, as well as for providing hair with conditioning effects such as good combability and hair control, the aforementioned detergents are generally blended with a cationic polymer compound obtained by introducing a quarternary nitrogen into a polymer compound such as cellulose, starch, natural rubber, diallyl compounds, polyacrylic acid compounds and polyvinyl compounds. However, at least about 0.2–0.5% by weight of a cationic polymer compound is required to be added to the detergent to obtain conditioning effects as described in SOFW Journal, vol. 120, p. 854, which arises a problem that such a large amount of a cationic polymer compound will cause tackiness and stiffness after drying.

It is known that a detergent having good foaming property and providing favorable feeling of use after washing can be obtained by using an amino acid-type active agent that provides pleasant feeling of use after washing, e.g., no stiffness, in combination with the aforementioned sulfate type surfactants, higher fatty acid salts or polyoxyethylene alkyl ether acetates (PCT/EP99/06113 and the like).

Further, International Patent Publication in Japanese (KOHYO) No. 9-506351 discloses a hair shampoo obtained by mixing a sulfate type surfactant with N-lauroylsarcosine sodium and cationized cellulose. Henkel has proposed a hair shampoo added with a polyoxyethylene alkyl ether sulfate, alkylglucoside, acylated hydrolyzed collagen and cationized cellulose ("Personal-Care Formulas" in Cosmetics & Toiletries, Allured Publishing Corp., 1997). By reducing an amount of cationized cellulose to 0.1%, these shampoos achieved excellent foaming property and improvement in combability after drying, whilst they successfully eliminated a problem of stiffness. However, the shampoos were not satisfactory in alleviation of creakiness during rinsing and achievement of moist and hair control after drying.

DISCLOSURE OF THE INVENTION

Accordingly, an object of the present invention is to solve the above problems and provide a detergent composition which has good foaming property and is free from squeak or friction during rinsing. Another object of the present invention is to provide a detergent composition with excellent feeling of use by imparting moistness to skin without tackiness, and providing hair with good control while suppressing stiffness and the like.

The inventors of the present invention conducted various studies to achieve the aforementioned objects. As a result, they found that a detergent composition which had a favorable foaming property and was free from creakiness or friction during rinsing was obtainable by adding an N-long-chain acyl acidic amino acid or a salt thereof to a composition containing at least one kind of surfactant selected from a group consisting of particular classes of anionic surfactants, amphoteric surfactants and nonionic surfactants and a cationic polymer compound. They also found that the resulting detergent composition had excellent feeling of use by imparting moistness to skin without tackiness and providing hair with repose while suppressing stiffness and the like. The present invention was achieved on the basis of these findings.

The present invention thus provides a detergent composition comprising:

(A) 5 to 30% by weight of at least one kind of surfactant selected from the group consisting of anionic surfactants, amphoteric surfactants, and nonionic surfactants based on the total weight of the composition;

(B) 0.1 to 5% by weight of a substance selected from the group consisting of N-long-chain acyl acidic amino acids and salts thereof based on the total weight of the composition; and (C) less than 0.2% by weight of a cationic polymer compound based on the total weight of the composition.

According to preferred embodiments of the aforementioned invention, provided are the aforementioned detergent composition, wherein the N-long-chain acyl acidic amino acids are N-long-chain acyl-glutamic acids; the aforementioned detergent composition, wherein the cationic polymer compound is quarternary-nitrogen containing cellulose ether; the aforementioned detergent composition, which contains a surfactant selected from the group consisting of alkylsulfates and alkyl ether sulfates as the anionic surfactant; the aforementioned detergent composition, which contains a surfactant selected from the group consisting of alkyl betaine-type surfactants and amidobetaine-type surfactants represented by the following formula (1) or (2):

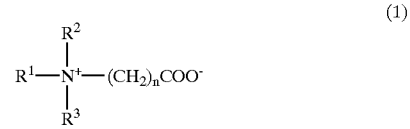

(1)

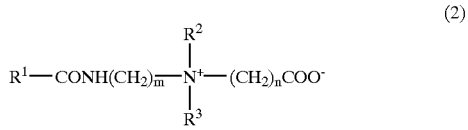

(2)

(in the formula, $R^1$ represents a linear or branched alkyl group having 5 to 21 carbon atoms or a linear or branched alkenyl group having 5 to 21 carbon atoms, $R^2$ and $R^3$ each independently represent a hydrogen atom or a linear or branched alkyl group having 1 to 3 carbon atoms, n represents an integer of from 1 to 3, and m represents an integer of from 1 to 4) as the amphoteric surfactant; the aforemen tioned detergent composition, which contains an alkyl polyglucoside represented by the following formula (3):

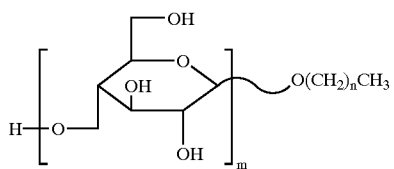

(in the formula, m represents an integer of from 1 to 5, and n represents an integer of from 7 to 19) as the nonionic surfactant; and the aforementioned detergent composition, wherein the acyl group in the N-long-chain acyl acidic amino acid is lauroyl group or a mixed acyl group containing lauroyl group.

PREFERRED EMBODIMENTS OF THE INVENTION

As the surfactant, a surfactant selected from a group consisting of anionic surfactants, amphoteric surfactants, and nonionic surfactants can be used. Various surfactants selected from said group can be used.

Examples of the anionic surfactants include sulfate ester-type anionic surfactants, amidoether-type anionic surfactants, sulfonic acid-type anionic surfactants, carboxylic acid-type anionic surfactants, sulfosuccinic acid-type anionic surfactants, isethionic acid-type anionic surfactants, N-acylamino acid-type anionic surfactants, phosphoric acid ester-type anionic surfactants and the like. Hydrophilic portions (hydrophilic functional groups) of these anionic surfactants can be used as soluble salts such as sodium salts, potassium salts, triethanolamine salts, ammonium salts, and basic amino acid salts. Among them, sulfate ester type anionic surfactants are preferred from a viewpoint of impartment of stability to a shampoo in a dissolved state. Particularly preferred examples include alkylsulfates and polyoxyethylene alkyl ether sulfates.

Examples of the amphoteric surfactants include alkyl betaine-type amphoteric surfactants, amidobetaine-type amphoteric surfactants, sulfobetaine-type amphoteric surfactants, phosphobetaine-type amphoteric surfactants, imidazoline-type amphoteric surfactants, proprionic acid-type surfactants, amine oxide-type amphoteric surfactants and the like. Among them, alkyl betaine-type amphoteric surfactants and amidobetaine type amphoteric surfactants are most preferably used in the present invention, because, when they are used in combination with the aforementioned sulfate ester-type anionic surfactants, they suppress stimulation of said surfactants and have an effect of imparting appropriate viscosity to a composition as a liquid detergent.

Preferred examples of the alkyl betaine-type amphoteric surfactants and the amidobetaine-type amphoteric surfactants include surfactants represented by the aforementioned formula (1) or (2). More specifically, preferred examples of the alkyl betaine-type amphoteric surfactants and the amidobetaine-type amphoteric surfactants include betaine lauryldimethylaminoacetate, cocobetaine, laurylamidopropylbetaine, cocoamidepropylbetaine, myristylamidopropylbetaine and the like.

Examples of the nonionic surfactants include, for example, alkylpolyglucosides represented by the aforementioned formula (3). More specifically, preferred examples of the alkylpolyglucoside include laurylglucoside, decylglucoside, coconut oil alkylglucoside, myristylglucoside and the like.

The surfactant selected from the group consisting of anionic surfactants, amphoteric surfactants and nonionic surfactants may be used alone, or two or more kinds of the surfactants may be used in combination. An amount of the surfactant is not particularly limited. For example, the amount may preferably be 5 to 30% by weight based on the total weight of the composition. When the amount is less than 5% by weight, foaming and cleansing properties and the like may sometimes be insufficient, and when the amount is higher than 30% by weight, ease of handling as a liquid detergent may sometimes be deteriorated.

As the long-chain acyl group constituting the N-long-chain acyl acidic amino acid, a linear or branched acyl group having 6 to 22 carbon atoms can be used, and the hydrocarbon chain may be either saturated or unsaturated. When the acyl group is unsaturated, two or more unsaturated bonds may be contained, and the unsaturated bonds may be either conjugated or not conjugated. Examples of the acyl group include, for example, acyl groups that can be derived from caproic acid, caprylic acid, capric acid, lauric acid, myristic acid, palmitic acid, stearic acid, behenic acid, linolic acid, linoleic acid, oleic acid, isostearic acid, 2-ethylhexanoic acid, coconut oil fatty acid, tallow fatty acid, hydrogenated tallow fatty acid and the like.

Among them, acyl groups having 8 to 18 carbon atoms are more preferred, and examples thereof include capryloyl group, caprinoyl group, lauroyl group, myristyl group, palmitoyl group, stearoyl group, coconut oil fatty acid acyl group (cocoyl group), hydrogenated tallow fatty acid acyl group, palm kernel oil fatty acid acyl group and the like. A particularly preferred acyl group is lauroyl group or a mixed acyl group containing lauroyl group. In the specification, a mixed acyl group means a mixture of acyl groups with different lengths of chains. For example, a coconut oil fatty acid acyl group is a mixed acyl group consisting of acyl groups including octanoyl group, decanoyl group, lauroyl group, myristoyl group, palmitoyl group and the like. When an acyl group having 6 or less carbon atoms is used, foaming and cleansing properties as a detergent may sometimes be insufficient, and when an acyl group having 22 or more carbon atoms is used, solubility of the substance into the detergent composition may be insufficient, thereby long-term stability may sometimes be lowered.

Examples of the acidic amino acids constituting the N-long-chain acyl acidic amino acids include glutamic acid and aspartic acid. Among them, glutamic acid is preferred from a viewpoint of stability against hydrolysis. As the acidic amino acid, either an optically active substance or a racemate may be used. Types of salts of the N-long-chain acyl acidic amino acids are not particularly limited. Examples of the salts include sodium salt, magnesium salt, potassium salt, ammonium salt, diethanolamine salt, thriethanolamine salt, arginine salt, lysine salt and the like.

Examples of the N-long-chain acyl acidic amino acids and salts thereof include N-long-chain acyl-glutamic acids and salts thereof such as N-coconut oil fatty acid acyl glutamic acids and salts thereof, N-lauroylglutamic acid and salts thereof, N-myristoylglutamic acid and salts thereof, N-palmitoylglutamic acid and salts thereof and N-oleoylglutamic acid and salts thereof, N-long-chain acyl-aspartic acids and salts thereof such as N-coconut oil fatty acid acyl aspartic acids and salts thereof and N-lauroylaspartic acid or salts thereof and the like. Among them, particularly preferred examples include N-coconut oil fatty acid acyl glutamic acids and salts thereof and N-lauroylglutamic acid and salts thereof. Most preferred examples include N-coconut oil fatty acid acyl glutamic acid salts and N-lauroylglutamic acid salts. Two or more kinds of N-long-chain acyl acidic amino acids or salts thereof may be used in combination.

An amount of N-long-chain acyl acidic amino acid or a salt thereof is not particularly limited. The amount may preferably be 0.1 to 5% by weight based on the total weight of the composition. When the amount is less than 0.1% by weight, sufficient effects may not be expected as to alleviation of creakiness during rinsing or impartation of repose and moistness after drying. When the amount is more than 5% by weight, foaming property may be deteriorated. The N-long-chain acyl acidic amino acids can be prepared by a know method, for example, the so-called Schotten-Bauman reaction in which a long-chain fatty acid halide and an amino acid are allowed to react in the presence of a basic catalyst (see, Japanese Patent Publication (Kokoku) No. 51-38681 and the like).

Type of the cationic polymer compound is not particularly limited so long as the polymer has a cationic functional group in the molecule. Examples include, for example, polymer compounds, e.g., cellulose, starch, natural rubbers, acrylic acid type, vinyl type and peptides, which are introduced with quarternary nitrogen. Examples include quarternary-nitrogen containing cellulose ethers (cationic celluloses), cationized guar gum, polymerization products of diallyl quarternary ammonium salt, cationic vinyl polymers such as polyvinylpyrrolidone, peptide derivatives such as cationized hydrolyzed proteins and the like.

As the cationic polymer compound, most preferred examples include quarternary-nitrogen containing cellulose ethers (cationized cellulose). These polymers are commercially available as UCARE POLYMER JR or LR series (Amerchol), Leogard G or L series (Akzo) and the like. As for impartation of moistness and repose of hair after drying, they can provide the most preferred results. Two or more kinds of cationic polymer compounds may be used in combination. An amount of the cationic polymer compound is not particularly limited. For example, an amount may be less than 0.2% by weight based on the total weight of the composition. When the amount is 0.2% by weight or more, tackiness of skin, stiffness of hair or the like may occur after drying. Lower limit of the amount is not particularly limited, however, the amount may be at least about 0.01% to obtain sufficient effects.

Applications of the detergent composition of the present invention are not particularly limited. For example, the composition can be preferably used as a detergent such as body shampoo, hair shampoo, face wash detergent and hand wash detergent. Further, the form of the detergent composition of the present invention is not particularly limited. In general, the composition can be prepared as a composition in a form of a liquid such as a composition containing water.

The detergent composition of the present invention can be added with various additives as optional ingredients which are usually used in detergent compositions, in addition to the aforementioned ingredients, so long as advantageous effects of the present invention are not lowered. The additives can be appropriately chosen by those skilled in the art depending on desired characteristics. Types of the additives are not particularly limited. Examples include, for example, materials described in the Japanese Standards of Cosmetic Ingredients, the Comprehensive Licensing Standards of Cosmetics by Category, the Japanese Standards of Quasi-Drugs, the Japanese Pharmacopoeia and the Japan's Specifications and Standards for Food Additives, such as oily materials for cosmetics, silicone compounds, inorganic and organic salts, polymer thickeners, hydrolyzed proteins, fatty acids, alcohols, polyhydric alcohols, extracts, amino acids, silicic acids, vitamins, enzymes, anti-inflammatory agents, antibacterial agents, antiseptics, antioxidants, ultraviolet absorbers, chelating agents, antiperspirants, pigments, dyes, oxidation dyes, organic and inorganic powders, pH regulators, pearling agents, moistening agents, humectants and the like.

EXAMPLES

The present invention will be explained more specifically with reference to the following examples. However, the scope of the present invention is not limited to these examples.

Examples 1–10

Preparation of Detergent Compositions

Liquid detergent compositions each having constitution shown in the following Tables 1 and 2 (active ingredients are shown in % by weight based on the total weight of 100%) were prepared in a conventional manner. These liquid detergents were used by a panel of 5 experts to perform sensory evaluation. For hand washing, (a) friction during rinsing, (b) moistness after drying, and (c) tackiness after drying were evaluated. For hair washing, (a) creakiness during rinsing, (b) repose after drying and (c) stiffness after drying were evaluated. For the sensory evaluation, average values of scores according to the criteria shown below were calculated, and an average value of 3.5 or higher was determined as good (○), 2.4–3.4 as normal (Δ), and less than 2.4 as poor (x).

<Criteria for skin sensory evaluation>

(a) Friction during rinsing

5: No friction
4: Little friction
3: Normal
2: Slightly strong friction
1: Very strong friction (b) Moistness after drying 5: Much moistness
4: Slight moistness
3: Normal
2: Little moistness
1: No moistness (c) Tackiness after drying 5: No tackiness
4: Little tackiness
3: Normal
2: Slight tackiness
1: Much tackiness -continued <Criteria for hair sensory evaluation>

(a) Squeak during rinsing

5: No squeak
4: Little squeak
3: Normal
2: Slightly strong squeak
1: Very strong squeak (b) Control of hair after drying 5: Very good control
4: Fairly good control
3: Normal
2: Slightly unfavorable control
1: Unfavorable control (c) Stiffness after drying 5: No stiffness
4: Little stiffness
3: Normal
2: Slight stiffness
1: Much stiffness From the results shown in Table 2, it was found that the detergent compositions of the present invention (compositions referred to as "examples") were more excellent in less sliminess during rinsing and favorable repose without stiffness after drying compared with compositions of the comparative examples.

Examples 11–15

Preparations of Body Shampoos

Body shampoos each having the constitution shown in the following Table 3 (amounts of active ingredients are shown in % by weight based on the total weight of 100%) were prepared in a conventional manner. All of the body shampoos obtained were found to have good foaming property and cause no friction during rinsing, as well as have favorable moistness without tackiness after drying.

TABLE 1

|  | Comparative Examples |  |  |  |  |  |  | Examples |  |  |  |  |
|---|---|---|---|---|---|---|---|---|---|---|---|---|
|  | 1 | 2 | 3 | 4 | 5 | 6 | 7 | 1 | 2 | 3 | 4 | 5 |
| Sodium polyoxyethylene alkyl ether sulfate | 15.0 | 15.0 |  |  | 13.5 | 13.5 | 13.5 | 13.5 | 13.5 | 13.5 | 11.0 | 13.0 |
| Cocoamidepropylbetaine |  |  |  |  |  |  |  |  |  |  | 2.5 |  |
| Laurylpoyglucoside |  |  |  |  |  |  |  |  |  |  |  | 2.0 |
| Sodium N-cocoyl-L-glutamate |  |  | 15.0 | 15.0 |  |  | 1.5 | 1.5 | 1.5 | 1.5 | 1.5 | 1.5 |
| Sodium N-lauroylsarcosine |  |  |  |  | 1.5 |  |  |  |  |  |  |  |
| Acylated hydrolyzed collagen |  |  |  |  |  | 1.5 |  |  |  |  |  |  |
| Cationic cellulose | 0.3 | 0.1 | 0.3 | 0.1 | 0.1 | 0.1 | 0.2 | 0.1 | 0.05 | 0.025 | 0.1 | 0.1 |
| Purified water | q.s. | q.s. | q.s. | q.s. | q.s. | q.s. | q.s. | q.s. | q.s. | q.s. | q.s. | q.s. |
| Total | 100 | 100 | 100 | 100 | 100 | 100 | 100 | 100 | 100 | 100 | 100 | 100 |
| Friction during rinsing | Δ | X | ⊚ | Δ | Δ | Δ | ⊚ | ⊚ | ○ | ○ | ⊚ | ⊚ |
| Moistness after drying | Δ | X | ⊚ | ⊚ | X | ○ | ⊚ | ⊚ | ⊚ | ⊚ | ⊚ | ⊚ |
| Tackiness after drying | Δ | ○ | X | ○ | ○ | X | X | ⊚ | ⊚ | ⊚ | ⊚ | ⊚ |

From the results shown in Table 1, it was found that the detergent compositions of the present invention (compositions referred to as "examples") were more excellent in less sliminess during rinsing and more moistness without tackiness after drying compared with compositions of the comparative examples.

TABLE 2

|  | Comparative Examples |  |  |  |  |  |  | Examples |  |  |  |  |
|---|---|---|---|---|---|---|---|---|---|---|---|---|
|  | 8 | 9 | 10 | 11 | 12 | 13 | 14 | 6 | 7 | 8 | 9 | 10 |
| Sodium polyoxyethylene alkyl ether sulfate | 15.0 | 15.0 |  |  | 13.5 | 13.5 | 13.5 | 13.5 | 13.5 | 13.5 | 11.0 | 13.0 |
| Cocoamidepropylbetaine |  |  |  |  |  |  |  |  |  |  | 2.5 |  |
| Laurylpoyglucoside |  |  |  |  |  |  |  |  |  |  |  | 2.0 |
| Sodium N-cocoyl-L-glutamate |  |  | 15.0 | 15.0 |  |  | 1.5 | 1.5 | 1.5 | 1.5 | 1.5 | 1.5 |
| Sodium N-lauroylsarcosine |  |  |  |  | 1.5 |  |  |  |  |  |  |  |
| Acylated hydrolyzed collagen |  |  |  |  |  | 1.5 |  |  |  |  |  |  |
| Cationic cellulose | 0.3 | 0.1 | 0.3 | 0.1 | 0.1 | 0.1 | 0.2 | 0.1 | 0.05 | 0.025 | 0.1 | 0.1 |
| Purified water | q.s. | q.s. | q.s. | q.s. | q.s. | q.s. | q.s. | q.s. | q.s. | q.s. | q.s. | q.s. |
| Total | 100 | 100 | 100 | 100 | 100 | 100 | 100 | 100 | 100 | 100 | 100 | 100 |
| Creakiness during rinsing | Δ | X | ⊚ | Δ | Δ | Δ | ⊚ | ⊚ | ○ | ○ | ⊚ | ⊚ |
| Response after drying | Δ | X | ⊚ | ⊚ | X | ○ | ⊚ | ⊚ | ⊚ | ⊚ | ⊚ | ⊚ |
| Stiffness after drying | Δ | ○ | X | ○ | ○ | X | X | ⊚ | ⊚ | ⊚ | ⊚ | ⊚ |

TABLE 3

| | Examples | | | | |
|---|---|---|---|---|---|
| | 11 | 12 | 13 | 14 | 15 |
| Sodium polyoxyothylene dodecyl ether sulfate | 10.8 | 5.4 | 7 | 10 | — |
| Sodium polyoxyethylene myristyl ether sulfate | — | — | — | — | 7.3 |
| Cocoamidepropylbetaine | 1.8 | 3 | 2 | 1.8 | — |
| Decylpolyglucoside | — | — | — | — | 5 |
| Laurylpolyglucoside | — | — | — | — | — |
| Coconut oil alkyl-polyglucoside | — | — | 3 | — | — |
| Sodium N-cocoyl-L-glutamate | 1.5 | 4.5 | — | 2.25 | 3.5 |
| Triethanolamine N-lauroyl-L-giutamate | — | — | 5 | — | — |
| Polyoxyethylene (2) lauryl ether | 1.5 | — | — | — | 1 |
| Polyoxyethylene (3) lauryl ether | — | 2.75 | — | 0.5 | — |
| Polyoxyethylene (7) coconut oil fatty acid glyceride | 5 | — | — | — | — |
| Coconut oil fatty acid monoethanolamide | — | — | — | 1 | — |
| Monoisopropanolamide laurate | 1 | — | — | — | — |
| Cationic cellulose | 0.1 | 0.1 | — | 0.1 | — |
| Cationic guar gum | — | — | 0.1 | — | 0.1 |
| Ethylene glycol distearate | 2.5 | — | — | 2 | 1 |
| PEG-120 methylglucose dioleate | — | 0.5 | — | — | — |
| Sodium chloride | 2.3 | — | 2 | 1 | 2 |
| Purified water | q.s. | q.s. | q.s. | q.s. | q.s. |
| Total | 100 | 100 | 100 | 100 | 100 |

Examples 16–20

Preparations of Hair Shampoos

Hair shampoos each having the constitution shown in the following Table 4 (amounts of active ingredients are shown in % by weight based on the total weight as 100%) were prepared in a conventional manner. All of the body shampoos obtained were found to have good foaming property and cause no creakiness during rinsing, as well as provide favorable repose without stiffness after drying.

TABLE 4

| | Examples | | | |
|---|---|---|---|---|
| | 16 | 17 | 18 | 19 |
| Ammonium Laurylsulfate | — | — | 4.8 | — |
| Sodium polyoxyethylene dodecyl ether sulfate | 8.1 | 7 | — | 8.1 |
| Ammonium polyoxyethylene dodecyl ether sulfate | — | — | 4.2 | — |
| Cocobetaine | — | — | — | — |
| Cocoamidepropylbetaine | — | 2.7 | 3.6 | — |
| Caprylyl/caprylglucoside | — | 4 | — | — |
| Decylpolyglucoside | 7 | — | — | — |
| Laurylpolyglucoside | — | — | — | — |
| Sodium N-cocoyl-L-glutamate | 1.25 | — | 2 | 1 |
| Triethanolamine N-lauroyl-L-glutamate | — | 2.5 | — | — |
| Polyoxyethylene (3) lauryl ether | 1.5 | — | — | — |
| Polyoxyethylene (7) coconut oil fatty acid glyceride | — | — | — | — |
| Monoethanolamide laurate | — | — | 2 | 5 |
| Coconut oil fatty acid monoethanolamide | — | — | 2.5 | — |
| Cationic cellulose | 0.1 | 0.1 | — | — |
| Cationic guar gum | — | — | 0.1 | — |
| Dimethylallylammonium chloride/acrylamide copolymer | — | — | — | 0.1 |
| Dimethicone copolyol | — | — | 1 | — |
| Ethylene glycol distearate | — | — | — | 2 |
| PEG-120 methylglucose dioleate | — | 1.5 | — | — |
| Sodium chloride | 1.5 | 0.3 | — | 0.4 |
| Purified water | q.s. | q.s. | q.s. | q.s. |
| Total | 100 | 100 | 100 | 100 |

The detergent composition of the present invention is characterized to have good foaming property and cause no friction during rinsing, and provide excellent feeling of use by imparting moistness without tackiness to skin and providing hair with repose without stiffness and the like.

What is claimed is:

1. A detergent composition comprising:

(A) 5 to 30% by weight, based on the total weight of said composition, of at least one kind of a first surfactant selected from the group consisting of anionic surfactants, amphoteric surfactants, and nonionic surfactants;

(B) 0.1 to 5% by weight, based n the total weight of said composition, of a substance selected from the group consisting of N-long-chain acyl acidic amino acids and salts thereof; and (C) 0.01% to less than 0.2% by weight, based on the total weight of said composition, of a cationic polymer compound.

2. The detergent composition according to claim 1, wherein said N-long-chain acyl acidic amino acid is an N-long-chain acyl-glutamic acid.

3. The detergent composition according to claim 1, wherein said cationic polymer compound is quarternary-nitrogen containing cellulose ether.

4. The detergent composition according to claim 1, which comprises a surfactant selected from the group consisting of alkylsulfates and alkyl ether sulfates as said anionic surfactant.

5. The detergent composition according to claim 1, which comprises as said amphoteric surfactant a surfactant selected from the group consisting of alkyl betaine-type surfactants and amidobetaine type surfactants represented by the following formula (1) or (2):

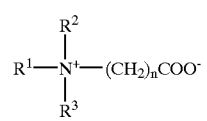

(1)

-continued

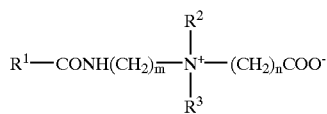
(2)

wherein R¹ represents a linear or branched alkyl group having 5 to 21 carbon atoms or a linear or branched alkenyl group having 5 to 21 carbon atoms; R² and R³ each independently represent a hydrogen atom or a linear or branched alkyl group having 1 to 3 carbon atoms; n represents an integer of from 1 t 3; and m represents an integer of from 1 to 4.

6. The detergent composition according to claim 1, which comprises as said nonionic surfactant an alkyl polyglucoside represented by the following formula (3):

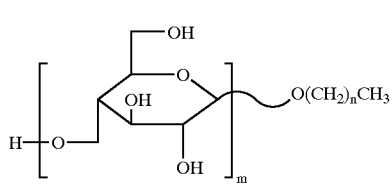
(3)

wherein m represents an integer of from 1 to 5 and n represents an integer of from 7 to 19.

7. The detergent composition according to claim 1, wherein the acyl group in said N-long-chain acyl acidic amino acid is a lauroyl group or a mixed acyl group comprising a lauroyl group.

8. The detergent composition according to claim 1, comprising said cationic polymer compound in an amount of 0.01 to 0.1, based on the total weight of said composition.

9. The detergent composition according to claim 1, comprising said cationic polymer compound in an amount of 0.01 to 0.05, based on the total weight of said composition.

10. The detergent composition according to claim 1, wherein said cationic polymer compound is selected from the group consisting of quarternary-nitrogen containing cellulose ethers, cationized guar gums, polymerization products of diallyl quarternary ammonium salts, cationic vinyl polymers, and cationized hydrolyzed proteins.

11. The detergent composition according to claim 1, comprising said N-long-chain acyl acidic amino acid in an amount of 1.5 to 4.5, based on the total weight of said composition.

12. The detergent composition according to claim 1, comprising said first surfactant in an amount of 12 t 30, based on the total weight of said composition.

13. The detergent composition according to claim 12, wherein said first surfactant is an anionic surfactant.

14. The detergent composition according to claim 12, wherein said first surfactant is an amphoteric surfactant.

15. The detergent composition according to claim 12, wherein said first surfactant is a nonionic surfactant.

16. The detergent composition according to claim 1, wherein said first surfactant is an anionic surfactant, said N-long-chain acyl acidic amino acid is an N-long-chain acyl-glutamic acid or salt hereof and said cationic polymer compound is a quarternary-nitrogen containing cellulose ether.

17. The detergent composition according to claim 16, wherein said anionic surfactant is selected from the group consisting of alkylsulfates and alkyl ether sulfates.

18. The detergent composition according to claim 1, wherein said first surfactant is an amphoteric surfactant, said N-long-chain acyl acidic amino acid is an N-long-chain acyl-glutamic acid or salt hereof and said cationic polymer compound is a quarternary-nitrogen containing cellulose ether.

19. The detergent composition according to claim 18, wherein said amphoteric surfactant is selected from the group consisting of alkyl betaine-type surfactants and amidobetaine type surfactants represented by the following formula (1) or (2):

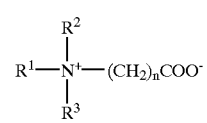
(1)

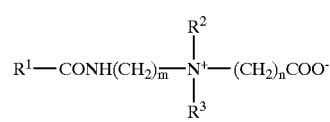
(2)

wherein R¹ represents a linear or branched alkyl group having 5 to 21 carbon atoms or a linear or branched alkenyl group having 5 to 21 carbon atoms; R² and R³ each independently represent a hydrogen atom or a linear or branched alkyl group having 1 to 3 carbon atoms; n represents an integer of from 1 to 3; and m represents an integer of from 1 to 4.

20. The detergent composition according to claim 1, wherein said nonionic surfactant is an alkyl polyglucoside represented by the following formula (3):

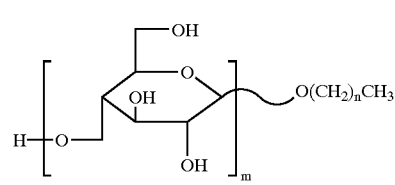
(3)

wherein m represents an integer of from 1 to 5 and n represents an integer of from 7 to 19.

21. The detergent composition according to claim 1, wherein said first surfactant is a nonionic surfactant, said N-long-chain acyl acidic amino acid is an N-long-chain acyl-glutamic acid or salt thereof and said cationic polymer compound is a quarternary-nitrogen containing cellulose ether.

* * * * *

UNITED STATES PATENT AND TRADEMARK OFFICE
CERTIFICATE OF CORRECTION

PATENT NO. : 6,656,892 B2
DATED : December 2, 2003
INVENTOR(S) : Eiko Oshimura

It is certified that error appears in the above-identified patent and that said Letters Patent is hereby corrected as shown below:

<u>Column 10,</u>
Line 38, "based n the total" should read -- based on the total --;
Line 50, "compound is quarternary-nitrogen" should read -- compound is a quaternary-nitrogen --.

<u>Column 11,</u>
Line 13, "from 1 t 3" should read -- from 1 to 3 --;
Line 51, "of 12 t 30" should read -- of 12 to 30 --.

<u>Column 12,</u>
Line 2, "or salt hereof" should read -- of salt thereof --;
Line 11, "or salt hereof" should read -- of salt thereof --.

Signed and Sealed this

Thirtieth Day of March, 2004

JON W. DUDAS
*Acting Director of the United States Patent and Trademark Office*